(12) United States Patent
McKeown

(10) Patent No.: US 9,422,511 B2
(45) Date of Patent: Aug. 23, 2016

(54) COMPOSITION FOR A CLEANER AND/OR FRESHENER COMPRISING VINEGAR, VANILLA EXTRACT, AND WITCH HAZEL

(71) Applicant: Margaret Mary McKeown, Markham (CA)

(72) Inventor: Margaret Mary McKeown, Markham (CA)

(73) Assignee: Captain and Malinker Incorporated, Markham, Ontario (CA)

( * ) Notice: Subject to any disclaimer, the term of this patent is extended or adjusted under 35 U.S.C. 154(b) by 0 days.

(21) Appl. No.: 14/523,026

(22) Filed: Oct. 24, 2014

(65) Prior Publication Data

US 2015/0119314 A1    Apr. 30, 2015

Related U.S. Application Data

(60) Provisional application No. 61/895,073, filed on Oct. 24, 2013.

(51) Int. Cl.
| | | |
|---|---|---|
| C11D 3/382 | (2006.01) |
| C11D 3/48 | (2006.01) |
| C11D 3/50 | (2006.01) |
| C11D 7/26 | (2006.01) |
| A61L 9/013 | (2006.01) |

(52) U.S. Cl.
CPC ........ *C11D 7/265* (2013.01); *A61L 9/013* (2013.01)

(58) Field of Classification Search
CPC ...... C11D 3/0068; C11D 3/0031; C11D 3/042; C11D 3/201; C11D 3/382; C11D 3/48; C11D 3/50; C11D 9/442; C11D 11/0017; C11D 17/0017
See application file for complete search history.

(56) References Cited

U.S. PATENT DOCUMENTS

| | | | | |
|---|---|---|---|---|
| 6,077,559 A * | 6/2000 | Logan | ............... | A23L 1/22058 426/533 |
| 2010/0034871 A1* | 2/2010 | Mikkelsen et al. | ............ | 424/440 |
| 2014/0030203 A1* | 1/2014 | Dombeck | ............ | 424/65 |
| 2014/0242198 A1* | 8/2014 | Modak et al. | ................. | 424/736 |
| 2015/0017312 A1* | 1/2015 | Tegel | ............... | 426/622 |

* cited by examiner

*Primary Examiner* — Charles Boyer

(57) ABSTRACT

A novel composition useful as a cleaner and/or freshener is provided comprising dilute acetic acid, pure vanilla extract, and optionally a natural scent component. A method of cleaning using the composition and a method of freshening using the composition is also provided.

13 Claims, No Drawings

COMPOSITION FOR A CLEANER AND/OR FRESHENER COMPRISING VINEGAR, VANILLA EXTRACT, AND WITCH HAZEL

TECHNICAL FIELD

The present disclosure generally relates to a novel composition for use as a cleaner and/or freshener, for example, to a natural composition for use as a cleaner and freshener.

BACKGROUND

So-called natural all-purpose cleaners and fresheners known in the art are, in fact, not all natural. Rather, these all-purpose cleaners and fresheners claiming to be natural are not completely free of harmful chemical components. Previous all-purpose cleaners and fresheners, even if largely comprised of natural ingredients, include at least one or more synthetic ingredients that result in an unknown or detrimental effect on the human body or the environment. These potentially harmful ingredients may include, for example, an amount of synthetic chemical for cleaning, emulsification, fragrance or stabilization. Additionally, due to the components of known all-purpose cleaners, these cleaners may leave behind an unpleasant odor that remains long after the cleaning process is complete.

Thus, it would be desirable to develop an alternative cleaner and/or freshener.

SUMMARY

In a first aspect of the invention, a composition is provided that comprises dilute acetic acid and pure vanilla extract.

In another aspect, a method of cleaning and freshening is provided comprising applying the composition to a surface to be cleaned.

In another aspect, a composition for freshening is provided comprising dilute acetic acid, pure vanilla extract, and a natural scent component.

A method of freshening is also provided comprising applying the composition for freshening to a surface, fabrics or the like.

In another aspect, a method of freshening is provided comprising diffusing the composition for air freshening.

These and other aspects of the invention will become apparent in the following detailed description and examples.

DETAILED DESCRIPTION

A composition for use as a cleaner and/or freshener is provided comprising dilute acetic acid, pure vanilla extract and optionally a natural scent component. In preferred aspects, the composition comprises natural ingredients. The cleaner and/or freshener may also comprise witch hazel distillate.

The present composition comprises dilute acetic acid, for example, a solution comprising about 5% to about 15% acetic acid by volume, and preferably about 5% to about 8% acetic acid by volume. In one embodiment, the dilute acetic acid is obtained by fermentation providing a natural component. For example, the dilute acetic acid may be a vinegar, for example a vinegar that is obtained by fermentation, e.g. fermentation of an organic substance such as fruits, vegetables and grains such as corn. The dilute acetic acid may, for example, be a white vinegar.

The composition may include witch hazel distillate. Witch hazel distillate is generally an extract from the leaves, twigs and/or bark of the Witch-hazel shrub (*Hamamelis virginiana*) that may contain compounds such as gallic acid, catechins, and flavonols such as kaempferol and quercetin, as well as natural chemicals found in its essential oil, e.g. carvacrol, eugenol, hexenol, choline and saponins. The actual composition of witch hazel distillate may vary depending on the source. However, for the purposes of the present invention, any witch hazel distillate is sufficient for use in the present composition. As one of skill in the art will appreciate, witch hazel distillate may be replaced by a functionally equivalent agent, e.g. an agent which exhibits the same or similar properties to a witch hazel distillate, such as an alcohol or other component within the witch hazel distillate. For example, a clear alcohol such as ethanol or ether may be used. Preferably, the functionally equivalent agent is also derived from a natural source.

As the cleaning agents, the combination of witch hazel distillate, if included, and dilute acetic acid may comprise at least about 45% by volume of the present composition. For example, the combination of the two ingredients may comprise about 46%, 47% or more of the total composition. In one embodiment, the combination of witch hazel distillate and dilute acetic acid comprises at least about 48% to about 50% by volume of the total composition. Accordingly, the dilute acetic acid, e.g. vinegar, may comprise between about 30% to about 45% of the total composition, and the witch hazel distillate may comprise between about 8% to about 20% of the total composition, to result in at least about 45% of the total composition. Alternatively, since witch hazel distillate is an optional ingredient, the dilute acetic acid may comprise about 45% or more by volume of the total composition.

The composition further comprises pure vanilla extract. Pure vanilla extract is a vanilla bean extract solution containing the flavor compound vanillin as the primary ingredient and is prepared by extracting processes in which vanilla beans are macerated or percolated in a solution of ethyl alcohol and water. Generally, in order for a vanilla extract to qualify as pure, it must contain a minimum amount of alcohol per vanilla bean content, for example, the U.S. Food and Drug Administration requires that pure vanilla extract contain a minimum 35% of alcohol and 100 g of vanilla beans per liter (13.35 ounces per gallon). As a result, pure vanilla extract may enhance cleaning properties of the present composition as well as provide a pleasant scent to the composition. Pure vanilla extract may comprise from about 0.01% to about 2% by volume of the present composition. As one of skill in the art will appreciate, double or triple strength pure vanilla extract may be used in the present composition. The amount of vanilla extract of a higher strength in the present composition may, thus, be adjusted accordingly. For example, double strength pure vanilla extract, made from 200 g of vanilla beans per liter alcohol, may be added to the composition in an amount at the lower end of the range.

The present composition may also comprise a natural scent component. The natural scent component will generally include an aqueous solution or colloidal suspension (hydrosol) of a fragrant essential oil obtained from an aromatic plant. Such solutions or suspensions may include herbal distillates, floral water, hydrosols, hydrolates, herbal water, essential water, essential oils, and combinations thereof. Examples of suitable natural scent solutions or suspensions include, but are not limited to, rose, orange flower, lemongrass, lavender, rose geranium, chamomile, sandalwood, rosemary, vanilla, pink grapefruit, ginger root, eucalyptus and the like.

The scent of the present composition may be enhanced by the addition of at least one concentrated plant essential oil such as mandarin orange, pink grapefruit, and lavender, among others, as will be appreciated by one skilled in the art. For example, a variety of floral waters and essential oils may be combined to create scents such as orange lemongrass, pink grapefruit, lavender vanilla or others. Various combinations of floral waters and essential oils may be included within the present composition as will be appreciated by one of skill in the art.

The balance, if required, of the present composition comprises water, for example, tap water, distilled water, spring water, or the like.

The natural scent and water components may comprise at least about 45% by volume of the total composition. The natural scent component may comprise about 20% to about 30% by volume of the present composition, and the water component may comprise between about 20% and about 30% by volume of the composition. The composition may optionally include about 0.01% to about 5% by volume of an essential oil.

As one of skill in the art will appreciate, one or more additional natural components may be added to the composition which function to facilitate its function as a cleaner or freshener, or which otherwise supplement the components within the composition. The amount of water in the composition may be adjusted to accommodate such additional components.

In one embodiment, the amount of each component in the present formulation may be as follows: about 30% to about 40% by volume of 5% vinegar and about 8% to about 20% of witch hazel distillate, the combination of which is at least about 45% by volume of the total composition; approximately equal parts of water and a natural scent component, for example, about 20-30% of water and about 20-30% of a natural scent component, the combination of which is at least about 45% by volume of the total composition; about 0.01% to about 5% of one or a mixture of essential oil by volume; and about 0.01% to about 2% of pure vanilla extract by volume. In a preferred embodiment, the composition comprises about 1.5 cups of 5% white vinegar, about 1 cup of one or a mixture of natural scent components, about 1 cup of water, about ½ cup witch hazel distillate, about 2 tablespoons of one or a mixture of essential oils and about 1 teaspoon (5 ml) of pure vanilla extract. Although this is an exemplary amount of each of the ingredients, the exemplary amounts may be adapted to different volumes while maintaining the ratio of each of the ingredients.

The present composition may be prepared by mixing the components together and then blending the mixture at, for example, an ultra high shear rate using an ultra high shear mixer operating at tip speeds of 11,000-18,000 feet per minute (fpm). The ultra high shear rate permits the composition to be subjected to higher levels of shear than a conventional rotor and stator combination providing reduced cycle time and greater efficiency to generate fine emulsions and dispersions. However, any conventional mixer or agitator may be used, for example, a conventional high shear mixer featuring a four-blade rotor running at a tip speed of about 3,000 to 4,000 fpm within a close tolerance fixed stator may be used. Because the composition is mechanically mixed and no stabilizers or chemical emulsifiers are used, the composition may separate over time requiring the user to shake the composition before use.

In another aspect of the present invention, a method of cleaning is also provided. For use as a cleaner, the present composition is applied to a surface to be cleaned, generally in an amount that covers the surface to be cleaned. For example, the composition may be applied using wipes pre-soaked with the present composition. Alternatively, the composition may be applied using a spray bottle or other dispensing means. Thus, the composition may be provided as a product within a container such as a spray bottle, a mop with a built-in mechanism for dispensing the composition, pre-soaked wipes, or other dispensing means as will be known to one skilled in the art. Optionally, the composition may have to be shaken prior to being applied to a surface in order to mix the ingredients that may have separated over time. Depending on the degree of cleaning required, more or less cleaner may be required in order to clean a given surface. Examples of surfaces that may be cleaned with the present composition include those that are non-porous such as stainless steel, mirrors, glass, slate, granite, sealed grout, porcelain, and various types of wood such as hardwood floors and laminate. Additionally, the composition may be used on vinyl, leather, and plastic. Use of the present composition on unsealed porous surfaces should be avoided, such as unsealed marble, as such surfaces may discolor. Following application, the composition may be wiped from the surface.

In another aspect of the invention, the present composition may be used for freshening or deodorizing in addition to or instead of cleaning. For example, the present composition may be provided in a spray bottle and sprayed into linens, curtains, bedding, furniture, carpets, or other fabrics and surfaces for freshening. Alternatively, the present composition may be provided in a container which is left open to freshen the air. In another embodiment, the composition may be used in a diffuser, in which reeds or other sticks may be placed into a container holding the composition, to diffuse the scent of the present composition into the air to freshen an area. It may alternatively be used in combination with a candle or burner for freshening. Other means of freshening and deodorizing are also contemplated as will be known to one skilled in the art.

Embodiments of the present invention are described in the following specific example which is not to be construed as limiting.

EXAMPLE

Formula

An example of a cleaning formula in accordance with an embodiment of the invention was prepared using the following ingredients in the amounts shown in Table 1. In the examples the pure vanilla extract used is Nielsen-Massey® Pure Bourbon Vanilla Extract, and the witch hazel distillate has between about 14% to about 15% alcohol.

TABLE 1

| Ingredient | Amount | mL | Percentage (%) in Final Solution (by vol) |
|---|---|---|---|
| Vinegar, 5% | 1.5 cup | 355 | 36 |
| Water | 1 cup | 237 | 24 |
| Witch Hazel Distillate | 0.5 cup | 118 | 12 |
| Pure Vanilla Extract | 1 tsp | 5 | 0.5 |
| Essential Oil | 2 tbsp | 30 | 3 |
| Floral Water | 1 cup | 237 | 24 |

The ingredients were combined and blended at an ultra high shear rate to produce a natural emulsification.

The composition was used to successfully clean a variety of surfaces, including counters, glass and stainless steel. The composition also possessed a pleasant scent that overshadowed the vinegar and witch hazel distillate odors.

The composition was also sprayed onto a variety of fabrics such as linens for freshening. It was additionally used as a diffuser to freshen the air.

While the foregoing example describes an embodiment of the present invention, it will be apparent to persons skilled in the art that a number of variations and modifications may be made without departing from the scope of the claims.

I claim:

1. A liquid composition comprising:
   vinegar in an amount ranging from about 30% to about 45% of the volume of the total composition, wherein the vinegar comprises about 5 to 8% acetic acid by volume;
   pure vanilla extract comprising at least 35% alcohol and vanillin from 100 g of vanilla beans per liter;
   witch hazel distillate or extract comprising about 8% to about 20% by volume of the total composition, and
   the balance of the composition is water.

2. The composition of claim 1, wherein the pure vanilla extract comprises about 0.01% to about 2% by volume of the total composition.

3. The composition of claim 1, further comprising a natural scent component selected from the group consisting of herbal distillates, floral water, hydrosols, hydrolates, herbal water, essential water and combinations thereof.

4. The composition of claim 3, wherein the natural scent component is selected from the group consisting of rose, orange flower, lemongrass, lavender, rose geranium, chamomile, sandalwood, rosemary, vanilla, pink grapefruit, ginger root, eucalyptus, mandarin orange, and combinations thereof.

5. The composition of claim 3, wherein the natural scent component comprises about 20% to about 30% by volume of the total composition.

6. The composition of claim 5, wherein the combination of water and the natural scent component comprises at least about 45% by volume of the total composition.

7. The composition of claim 1, further comprising an essential oil, wherein the essential oil comprises between about 0.01% to about 5% by volume of the total composition.

8. The composition of claim 7, wherein the essential oil is selected from the group consisting of rose, orange flower, lemongrass, lavender, rose geranium, chamomile, sandalwood, rosemary, vanilla, pink grapefruit, ginger root, eucalyptus, mandarin orange, and combinations thereof.

9. The composition of claim 1, further comprising a natural scent component in an amount ranging from about 20% to about 30% by volume of the total composition, and an essential oil in an amount ranging from about 0.01% to about 5% by volume of the total composition, and wherein the pure vanilla extract is in an amount ranging from about 0.01% to about 2% by volume of the total composition.

10. A method of cleaning comprising applying the composition of claim 1 to a surface to be cleaned and optionally wiping the surface.

11. A method of freshening comprising applying the composition of claim 1 to a surface or an area to be freshened and optionally wiping the surface to be freshened or diffusing the composition of claim 1.

12. A product comprising a container which holds a volume of the composition of claim 1.

13. A method of making the composition of claim 1, comprising:
    combining the pure vanilla extract, witch hazel distillate and vinegar to form a mixture; and
    mechanically blending the mixture at a high shear rate to produce an emulsion.

* * * * *